US008916386B2

(12) United States Patent
Hughes et al.

(10) Patent No.: US 8,916,386 B2
(45) Date of Patent: Dec. 23, 2014

(54) METHOD TO DETECT AND SEQUENCE POST TRANSLATIONALLY MODIFIED PEPTIDES

(75) Inventors: Christopher John Hughes, Manchester (GB); Therese McKenna, Preston (GB); David Gordon, Manchester (GB); Daniel James Kenny, Knutsford (GB)

(73) Assignee: Micromass UK Limited, Wilmslow (GB)

(*) Notice: Subject to any disclaimer, the term of this patent is extended or adjusted under 35 U.S.C. 154(b) by 241 days.

(21) Appl. No.: 13/375,124

(22) PCT Filed: May 28, 2010

(86) PCT No.: PCT/GB2010/001077
§ 371 (c)(1),
(2), (4) Date: Feb. 1, 2012

(87) PCT Pub. No.: WO2010/136780
PCT Pub. Date: Dec. 2, 2010

(65) Prior Publication Data
US 2012/0122077 A1 May 17, 2012

Related U.S. Application Data

(60) Provisional application No. 61/182,123, filed on May 29, 2009.

(30) Foreign Application Priority Data

May 29, 2009 (GB) .................................. 0909285.9

(51) Int. Cl.
*G01N 24/00* (2006.01)
*G01N 33/68* (2006.01)
*H01J 49/00* (2006.01)

(52) U.S. Cl.
CPC ........ *G01N 33/6848* (2013.01); *H01J 49/0045* (2013.01); *H01J 49/0031* (2013.01)

USPC .......................................... 436/173; 422/68.1

(58) Field of Classification Search
None
See application file for complete search history.

(56) References Cited

U.S. PATENT DOCUMENTS 7,548,818 B2   6/2009   Keiser
7,829,845 B2   11/2010  Deguchi et al.

OTHER PUBLICATIONS

Lenz, "*Detection of Protein-RNA Crosslinks by NanoLC-ESI-MS/MS Using Precursor Ion Scanning and Multiple Reaction Monitoring (MRM) Experiments*", Journal of American Society for Mass Spectrometry, vol. 18, pp. 869-881, Mar. 2007.
Williamson et al., "*Automated Identification and Quantification of Protein Phosphorylation Sites by LC/MS on a Hybrid Triple Quadrupole Linear Ion Trap Mass Spectrometer*", Molecular & Cellular Proteomics, vol. 5, No. 2, pp. 337-346, Oct. 2005.
Unwin et al., "*Multiple Reaction Monitoring to Identify Sites of Protein Phosphorylation with High Sensitivity*", Molecular & Cellular Proteomics, vol. 4, No. 8, pp. 1134-1144, May 2005.
Cox et al., "*Multiple Reaction Monitoring as a Method for Identifying Protein Posttranslational Modifications*", Journal of Biomolecular Techniques, vol. 16, No. 2, pp. 83-90, Jun. 2005.
Yocum et al., "*Current Affairs in Quantitative Targeted Proteomics: Multiple Reaction Monitoring-Mass Spectrometry*", Briefings in Functional Genomics and Proteomics, Vo. 8, No. 2, pp. 145-157, Mar. 2009.

*Primary Examiner* — Robert Xu
(74) *Attorney, Agent, or Firm* — Diederiks & Whitelaw, PLC (57) ABSTRACT

A method of detecting and sequencing post translationally modified peptides is disclosed wherein a negative ion precursor scan is performed. A negative ion high resolution MS scan is then performed and then MRM channels in positive ion mode are determined and monitored. A positive ion MS/MS scan is then performed.

7 Claims, 9 Drawing Sheets

Prior Art

METHOD TO DETECT AND SEQUENCE POST TRANSLATIONALLY MODIFIED PEPTIDES

CROSS-REFERENCE TO RELATED APPLICATIONS

This application represents a National stage application of PCT/GB2010/001077 entitled "Method to Detect and Sequence Post Translationally Modified Peptides" filed 28 May 2010 which claims priority to and benefit of U.S. Provisional patent application Ser. No. 61/182,123 filed on 29 May 2009 and United Kingdom Patent Application No. 0909285.9 filed on 29 May 2009. The entire contents of these applications are incorporated herein by reference.

BACKGROUND OF THE INVENTION

The present invention relates to the field of mass spectrometry and in particular to the detection and identification of post translationally modified peptides using a mass spectrometer.

Peptides consist of 20 commonly occurring amino acids that are linked together via amide bonds during the process of translating the mRNA message into protein sequence. The post translational modification of these polypeptides is ubiquitous and it is now widely understood and accepted that these modifications often infer biological function. There are a considerable number of modifications that occur, with common modifications including phosphorylation, glycosylation, myristylation, acetylation, methylation and ubiquinylation.

Tandem quadrupole mass spectrometers are widely used in a variety of industries. A known tandem quadrupole mass spectrometer comprises a first resolving quadrupole mass filter (MS1) followed by a gas filled collision cell arranged downstream of the first quadrupole mass filter. A second resolving quadrupole (MS2) is arranged downstream of the collision cell. Historically, the collision cell has often comprised a non-resolving quadrupole rod set leading to these instruments being known as "triple quadrupoles".

A common mode of operation of a tandem quadrupole mass spectrometer is known as Multiple Reaction Monitoring ("MRM"), wherein the first quadrupole mass filter MS1 is set to transmit only a pre-determined precursor or parent ion which is then fragmented in the collision cell. The resultant fragment ions are then transmitted to the second quadrupole mass analyser MS2 which is operated as a mass filter and is set so that only a single predetermined fragment ion is transmitted onwards to the ion detector. The resultant signal that is detected is therefore highly specific and highly sensitive.

Another common mode of operation of the known tandem quadrupole instrument is known as "precursor or parent ion scanning" wherein the first quadrupole mass filter MS1 is scanned across a chosen mass range with the transmitted ions being fragmented in the collision cell. The second quadrupole mass filter MS2 is set to transmit a fixed fragment mass. The resultant mass spectrum contains only those precursor or parent ions that fragmented to give the chosen fragment ion. Again, this is a highly specific and sensitive mode of operation.

A further mode of operation is known as "daughter or product ion scanning" or MS/MS wherein the first quadrupole MS1 is set to transmit a chosen precursor or parent ion which is subsequently fragmented in the collision cell. The second quadrupole mass filter MS2 is then scanned across a chosen mass range to allow a mass spectrum of the daughter or product ions to be acquired.

A MS scan is where either MS1 is set to resolve and is scanned with MS2 not resolving or vice versa. A MS scan generates a spectrum of all of the parent or precursor ions.

Several MS based approaches to the detection and sequencing of PTM peptides are known. These incorporate both infusion based and liquid chromatography based separation strategies, in combination with a variety of MS instrument geometries, such a tandem quadrupole systems and hybrid quadrupole-Time of Flight mass analyser systems. It is known, for example, to use precursor ion scanning looking for a common structural motif on a tandem quadrupole based system. However, there are several problems with the known approaches. Increasingly, the approaches have to be compatible with nanoscale liquid chromatography separations having narrow peak widths (of between 4-10 seconds). This demands that a complete analytical cycle of the experiment take no longer than one second to ensure adequate points across the chromatographic peak. This is not true of most known approaches. Secondly, brute force approaches have been used to try and sequence all peptides and sort the modified peptides from the non-modified peptides. This is highly time consuming and involves acquiring a considerable amount of redundant MS/MS information.

A specific, rapid technique with high sensitivity is desirable to detect and characterise post translationally modified peptides.

It is therefore desired to provide an improved mass spectrometer and method of mass spectrometry.

SUMMARY OF THE INVENTION

According to an aspect of the present invention there is provided a method of mass spectrometry comprising:

providing a mass spectrometer comprising an ion source, a mass filter or mass analyser, a collision, fragmentation or reaction device arranged downstream of the first mass filter or mass analyser and a second mass filter or mass analyser arranged downstream of the collision, fragmentation or reaction device;

performing a relatively low resolution negative parent ion scan wherein a mass to charge ratio transmission window of the first mass filter or mass analyser is scanned whilst a mass to charge ratio transmission window of the second mass filter or mass analyser is fixed and monitoring for first fragment ions of interest having a first mass to charge ratio;

wherein if first fragment ions of interest are detected then the method further comprises:

(i) performing a relatively high resolution negative MS scan wherein a mass to charge ratio transmission window of either the first mass filter or mass analyser or the second mass filter or mass analyser is scanned whilst the other mass filter or mass analyser is operated in a non-resolving mode of operation;

(ii) determining at least a first positive ion Multiple Reaction Monitoring channel corresponding to positive ions having a first positive charge state, a second positive ion Multiple Reaction Monitoring channel corresponding to positive ions having a second positive charge state and a third positive ion Multiple Reaction Monitoring channel corresponding to positive ions having a third positive charge state;

(iii) setting and monitoring at least the first, second and third positive ion Multiple Reaction Monitoring channels and determining which Multiple Reaction Monitoring channel results in the highest intensity of observed ions;

(iv) determining the mass to charge ratio and/or charge state of parent ions which correspond with the Multiple Reaction Monitoring channel which resulted in the highest intensity of observed ions; and (v) performing a MS/MS scan wherein a mass to charge ratio transmission window of the first mass filter or mass analyser is set so as to correspond with the mass to charge ratio transmission window at which the first mass filter or mass analyser was set for the Multiple Reaction Monitoring channel which resulted in the highest intensity of observed ions, and wherein a mass to charge ratio transmission window of the second mass filter or mass analyser is scanned.

According to another aspect of the present invention there is provided a method of mass spectrometry comprising:

providing a mass spectrometer comprising an ion source, a mass filter or mass analyser, a collision, fragmentation or reaction device arranged downstream of the first mass filter or mass analyser and a second mass filter or mass analyser arranged downstream of the collision, fragmentation or reaction device;

performing a relatively low resolution negative ion neutral loss or gain scan wherein a mass to charge ratio transmission window of the first mass filter or mass analyser is scanned whilst a mass to charge ratio transmission window of the second mass filter or mass analyser is scanned in synchronism with the first mass filter or mass analyser and monitoring for first fragment ions of interest having a first mass to charge ratio difference;

wherein if first fragment ions of interest are detected then the method further comprises:

(i) performing a relatively high resolution negative MS scan wherein a mass to charge ratio transmission window of either the first mass filter or mass analyser or the second mass filter or mass analyser is scanned whilst the other mass filter or mass analyser is operated in a non-resolving mode of operation;

(ii) determining at least a first positive ion Multiple Reaction Monitoring channel corresponding to positive ions having a first positive charge state, a second positive ion Multiple Reaction Monitoring channel corresponding to positive ions having a second positive charge state and a third positive ion Multiple Reaction Monitoring channel corresponding to positive ions having a third positive charge state;

(iii) setting and monitoring at least the first, second and third positive ion Multiple Reaction Monitoring channels and determining which Multiple Reaction Monitoring channel results in the highest intensity of observed ions;

(iv) determining the mass to charge ratio and/or charge state of parent ions which correspond with the Multiple Reaction Monitoring channel which resulted in the highest intensity of observed ions; and (v) performing a MS/MS scan wherein a mass to charge ratio transmission window of the first mass filter or mass analyser is set so as to correspond with the mass to charge ratio transmission window at which the first mass filter or mass analyser was set for the Multiple Reaction Monitoring channel which resulted in the highest intensity of observed ions, and wherein a mass to charge ratio transmission window of the second mass filter or mass analyser is scanned.

According to another less preferred aspect of the present invention there is provided a method of mass spectrometry comprising:

providing a mass spectrometer comprising an ion source, a mass filter or mass analyser, a collision, fragmentation or reaction device arranged downstream of the first mass filter or mass analyser and a second mass filter or mass analyser arranged downstream of the collision, fragmentation or reaction device;

performing a relatively low resolution positive parent ion scan wherein a mass to charge ratio transmission window of the first mass filter or mass analyser is scanned whilst a mass to charge ratio transmission window of the second mass filter or mass analyser is fixed and monitoring for first fragment ions of interest having a first mass to charge ratio;

wherein if first fragment ions of interest are detected then the method further comprises:

(i) performing a relatively high resolution positive MS scan wherein a mass to charge ratio transmission window of either the first mass filter or mass analyser or the second mass filter or mass analyser is scanned whilst the other mass filter or mass analyser is operated in a non-resolving mode of operation;

(ii) determining at least a first negative ion Multiple Reaction Monitoring channel corresponding to negative ions having a first negative charge state, a second negative ion Multiple Reaction Monitoring channel corresponding to negative ions having a second negative charge state and a third negative ion Multiple Reaction Monitoring channel corresponding to negative ions having a third negative charge state;

(iii) setting and monitoring at least the first, second and third negative ion Multiple Reaction Monitoring channels and determining which Multiple Reaction Monitoring channel results in the highest intensity of observed ions;

(iv) determining the mass to charge ratio and/or charge state of parent ions which correspond with the Multiple Reaction Monitoring channel which resulted in the highest intensity of observed ions; and (v) performing a MS/MS scan wherein a mass to charge ratio transmission window of the first mass filter or mass analyser is set so as to correspond with the mass to charge ratio transmission window at which the first mass filter or mass analyser was set for the Multiple Reaction Monitoring channel which resulted in the highest intensity of observed ions, and wherein a mass to charge ratio transmission window of the second mass filter or mass analyser is scanned.

According to another less preferred aspect of the present invention there is provided a method of mass spectrometry comprising:

providing a mass spectrometer comprising an ion source, a mass filter or mass analyser, a collision, fragmentation or reaction device arranged downstream of the first mass filter or mass analyser and a second mass filter or mass analyser arranged downstream of the collision, fragmentation or reaction device;

performing a relatively low resolution positive ion neutral loss or gain scan wherein a mass to charge ratio transmission window of the first mass filter or mass analyser is scanned whilst a mass to charge ratio transmission window of the second mass filter or mass analyser is scanned in synchronism with the first mass filter or mass analyser and monitoring for first fragment ions of interest having a first mass to charge ratio difference;

wherein if first fragment ions of interest are detected then the method further comprises:

(i) performing a relatively high resolution positive MS scan wherein a mass to charge ratio transmission window of either the first mass filter or mass analyser or the second mass filter or mass analyser is scanned whilst the other mass filter or mass analyser is operated in a non-resolving mode of operation;

(ii) determining at least a first negative ion Multiple Reaction Monitoring channel corresponding to negative ions having a first negative charge state, a second negative ion Multiple Reaction Monitoring channel corresponding to negative ions having a second negative charge state and a third negative ion Multiple Reaction Monitoring channel corresponding to negative ions having a third negative charge state;

(iii) setting and monitoring at least the first, second and third negative ion Multiple Reaction Monitoring channels and determining which Multiple Reaction Monitoring channel results in the highest intensity of observed ions;

(iv) determining the mass to charge ratio and/or charge state of parent ions which correspond with the Multiple Reaction Monitoring channel which resulted in the highest intensity of observed ions; and (v) performing a MS/MS scan wherein a mass to charge ratio transmission window of the first mass filter or mass analyser is set so as to correspond with the mass to charge ratio transmission window at which the first mass filter or mass analyser was set for the Multiple Reaction Monitoring channel which resulted in the highest intensity of observed ions, and wherein a mass to charge ratio transmission window of the second mass filter or mass analyser is scanned.

The Multiple Reaction Monitoring channels are preferably arranged to have a mass to charge ratio width of x Da at half height, wherein x is selected from the group consisting of: (i) <0.1; (ii) 0.1-0.2; (iii) 0.2-0.3; (iv) 0.3-0.4; (v) 0.4-0.5; (vi) 0.5-0.6; (vii) 0.6-0.7; (viii) 0.7-0.8; (ix) 0.8-0.9; and (x) 0.9-1.0.

The method preferably further comprises ionising ions using an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; and (xviii) a Thermospray ion source.

According to an embodiment the method further comprises temporally separating analyte ions of interest using a liquid chromatography device prior to ionising the analyte ions using an ion source.

The collision, fragmentation or reaction device is preferably selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an ion-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; and (xxviii) an ion-metastable atom reaction device for reacting ions to form adduct or productions.

According to another aspect of the present invention there is provided a mass spectrometer comprising:

an ion source, a mass filter or mass analyser, a collision, fragmentation or reaction device arranged downstream of the first mass filter or mass analyser and a second mass filter or mass analyser arranged downstream of the collision, fragmentation or reaction device; and a control system arranged and adapted, to perform a relatively low resolution negative parent ion scan wherein a mass to charge ratio transmission window of the first mass filter or mass analyser is scanned whilst a mass to charge ratio transmission window of the second mass filter or mass analyser is fixed and monitoring for first fragment ions of interest having a first mass to charge ratio;

wherein if first fragment ions of interest are detected then the control system further:

(i) performs a relatively high resolution negative MS scan wherein a mass to charge ratio transmission window of either the first mass filter or mass analyser or the second mass filter or mass analyser is scanned whilst the other mass filter or mass analyser is operated in a non-resolving mode of operation;

(ii) determines at least a first positive ion Multiple Reaction Monitoring channel corresponding to positive ions having a first positive charge state, a second positive ion Multiple Reaction Monitoring channel corresponding to positive ions having a second positive charge state and a third positive ion Multiple Reaction Monitoring channel corresponding to positive ions having a third positive charge state;

(iii) sets and monitors at least the first, second and third positive ion Multiple Reaction Monitoring channels and determining which Multiple Reaction Monitoring channel results in the highest intensity of observed ions;

(iv) determines the mass to charge ratio and/or charge state of parent ions which correspond with the Multiple Reaction Monitoring channel which resulted in the highest intensity of observed ions; and (v) performs a MS/MS scan wherein a mass to charge ratio transmission window of the first mass filter or mass analyser is set so as to correspond with the mass to charge ratio transmission window at which the first mass filter or mass analyser was set for the Multiple Reaction Monitoring channel which resulted in the highest intensity of observed ions, and wherein a mass to charge ratio transmission window of the second mass filter or mass analyser is scanned.

According to another aspect of the present invention there is provided a mass spectrometer comprising:

an ion source, a mass filter or mass analyser, a collision, fragmentation or reaction device arranged downstream of the first mass filter or mass analyser and a second mass filter or mass analyser arranged downstream of the collision, fragmentation or reaction device; and a control system arranged and adapted to perform a relatively low resolution negative ion neutral loss or gain scan wherein a mass to charge ratio transmission window of the first mass filter or mass analyser is scanned whilst a mass to charge ratio transmission window of the second mass filter or mass analyser is scanned in synchronism with the first mass filter or mass analyser and monitoring for first fragment ions of interest having a first mass to charge ratio difference;

wherein if first fragment ions of interest are detected then the control system further:

(i) performs a relatively high resolution negative MS scan wherein a mass to charge ratio transmission window of either the first mass filter or mass analyser or the second mass filter or mass analyser is scanned whilst the other mass filter or mass analyser is operated in a non-resolving mode of operation;

(ii) determines at least a first positive ion Multiple Reaction Monitoring channel corresponding to positive ions having a first positive charge state, a second positive ion Multiple Reaction Monitoring channel corresponding to positive ions having a second positive charge state and a third positive ion Multiple Reaction Monitoring channel corresponding to positive ions having a third positive charge state;

(iii) sets and monitors at least the first, second and third positive ion Multiple Reaction Monitoring channels and determining which Multiple Reaction Monitoring channel results in the highest intensity of observed ions;

(iv) determines the mass to charge ratio and/or charge state of parent ions which correspond with the Multiple Reaction Monitoring channel which resulted in the highest intensity of observed ions; and (v) performs a MS/MS scan wherein a mass to charge ratio transmission window of the first mass filter or mass analyser is set so as to correspond with the mass to charge ratio transmission window at which the first mass filter or mass analyser was set for the Multiple Reaction Monitoring channel which resulted in the highest intensity of observed ions, and wherein a mass to charge ratio transmission window of the second mass filter or mass analyser is scanned.

According to another less preferred aspect of the present invention there is provided a mass spectrometer comprising:

an ion source, a mass filter or mass analyser, a collision, fragmentation or reaction device arranged downstream of the first mass filter or mass analyser and a second mass filter or mass analyser arranged downstream of the collision, fragmentation or reaction device; and a control system arranged and adapted to perform a relatively low resolution positive parent ion scan wherein a mass to charge ratio transmission window of the first mass filter or mass analyser is scanned whilst a mass to charge ratio transmission window of the second mass filter or mass analyser is fixed and monitoring for first fragment ions of interest having a first mass to charge ratio;

wherein if first fragment ions of interest are detected then the control system further:

(i) performs a relatively high resolution positive MS scan wherein a mass to charge ratio transmission window of either the first mass filter or mass analyser or the second mass filter or mass analyser is scanned whilst the other mass filter or mass analyser is operated in a non-resolving mode of operation;

(ii) determines at least a first negative ion Multiple Reaction Monitoring channel corresponding to negative ions having a first negative charge state, a second negative ion Multiple Reaction Monitoring channel corresponding to negative ions having a second negative charge state and a third negative ion Multiple Reaction Monitoring channel corresponding to negative ions having a third negative charge state;

(iii) sets and monitors at least the first, second and third negative ion Multiple Reaction Monitoring channels and determining which Multiple Reaction Monitoring channel results in the highest intensity of observed ions;

(iv) determines the mass to charge ratio and/or charge state of parent ions which correspond with the Multiple Reaction Monitoring channel which resulted in the highest intensity of observed ions; and (v) performs a MS/MS scan wherein a mass to charge ratio transmission window of the first mass filter or mass analyser is set so as to correspond with the mass to charge ratio transmission window at which the first mass filter or mass analyser was set for the Multiple Reaction Monitoring channel which resulted in the highest intensity of observed ions, and wherein a mass to charge ratio transmission window of the second mass filter or mass analyser is scanned.

According to another less preferred aspect of the present invention there is provided a mass spectrometer comprising:

an ion source, a mass filter or mass analyser, a collision, fragmentation or reaction device arranged downstream of the first mass filter or mass analyser and a second mass filter or mass analyser arranged downstream of the collision, fragmentation or reaction device; and a control system arranged and adapted to perform a relatively low resolution positive ion neutral loss or gain scan wherein a mass to charge ratio transmission window of the first mass filter or mass analyser is scanned whilst a mass to charge ratio transmission window of the second mass filter or mass analyser is scanned in synchronism with the first mass filter or mass analyser and monitoring for first fragment ions of interest having a first mass to charge ratio difference;

wherein if first fragment ions of interest are detected then the control system further:

(i) performs a relatively high resolution positive MS scan wherein a mass to charge ratio transmission window of either the first mass filter or mass analyser or the second mass filter or mass analyser is scanned whilst the other mass filter or mass analyser is operated in a non-resolving mode of operation;

(ii) determines at least a first negative ion Multiple Reaction Monitoring channel corresponding to negative ions having a first negative charge state, a second negative ion Multiple Reaction Monitoring channel corresponding to negative ions having a second negative charge state and a third negative ion Multiple Reaction Monitoring channel corresponding to negative ions having a third negative charge state;

(iii) sets and monitors at least the first, second and third negative ion Multiple Reaction Monitoring channels and determining which Multiple Reaction Monitoring channel results in the highest intensity of observed ions;

(iv) determines the mass to charge ratio and/or charge state of parent ions which correspond with the Multiple Reaction Monitoring channel which resulted in the highest intensity of observed ions; and (v) performs a MS/MS scan wherein a mass to charge ratio transmission window of the first mass filter or mass analyser is set so as to correspond with the mass to charge ratio transmission window at which the first mass filter or mass analyser was set for the Multiple Reaction Monitoring channel which resulted in the highest intensity of observed ions, and wherein a mass to charge ratio transmission window of the second mass filter or mass analyser is scanned.

The mass spectrometer preferably further comprises an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; and (xviii) a Thermospray ion source.

According to an embodiment the mass spectrometer further comprises:

one or more ion guides; and/or one or more ion mobility separation devices and/or one or more Field Asymmetric Ion Mobility Spectrometer devices; and/or one or more ion traps or one or more ion trapping regions.

The collision, fragmentation or reaction device is preferably selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an ion-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; and (xxviii) an ion-metastable atom reaction device for reacting ions to form adduct or product ions.

The preferred embodiment of the present invention relates to a method which utilises mass spectrometry and which can be used to detect and then sequence the site of post translational modification on a peptide. The method preferably incorporates analysis of the protein sample by liquid chromatography in combination with mass spectrometry using a combination of different scan modes in order: (i) to determine when a PTM peptide is present; (ii) to determine the mass to charge ratio and charge state of the modified peptide; and (iii) subsequently to determine structural information so as to pinpoint the location of the modification within the amino acid sequence.

According to an embodiment of the present invention a method is disclosed wherein:

a precursor ion scan is performed in negative ion mode to identify negatively charged precursors which fragment to give a specific fragment ion;

an optional high mass resolution negative ion scan is performed on any identified precursors to accurately determine their mass and charge state;

multiple MRM channels are determined to monitor in positive ion mode to identify the most intense positive ion and charge state of the previously identified negatively charged precursor; and a product ion or MS/MS scan is performed on the identified precursor.

According to the preferred embodiment the most abundant charge state of the positive ion is identified rather than assuming that it will be the same charge state as in negative ion mode.

BRIEF DESCRIPTION OF THE DRAWINGS

Various embodiments of the present invention will now be described, by way of example only, and with reference to the accompanying drawings in which.

DETAILED DESCRIPTION OF THE INVENTION

Figure 1:
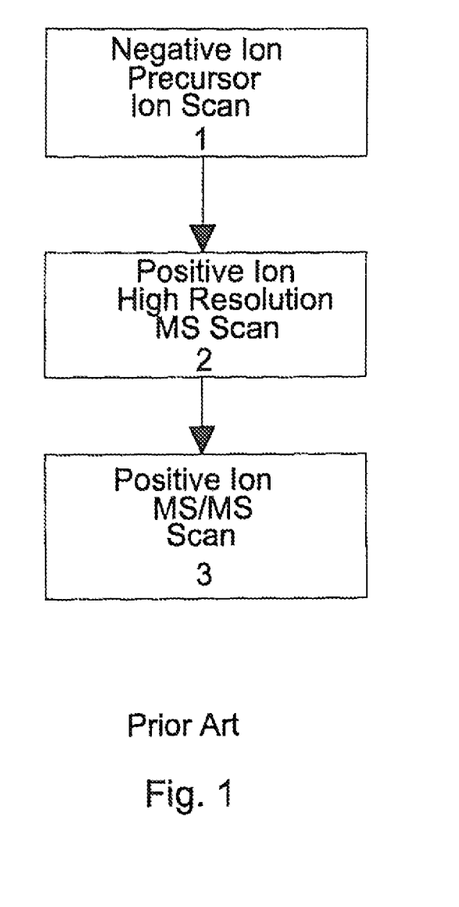
FIG. 1 shows a conventional method of identifying and characterising post translationally modified peptides.

A conventional method of identifying and characterising post translationally modified peptides is shown in FIG. 1 and comprises performing a relatively low resolution negative ion precursor or parent ion scan to identify parent ions which give rise to negatively charged fragment ions having a particular mass to charge ratio of interest. A high resolution positive ion MS scan 2 is then performed to determine accurately the mass to charge ratio of corresponding positively charged parent ions of interest. A positive ion MS/MS scan 3 is then performed in order to identify the parent ions of interest.

According to the conventional technique if singly charged negative parent ions are determined to be of interest then it is assumed that the corresponding positively charged parent ions are also singly charged. However, this assumption may not be correct. According to the preferred embodiment as detailed below this assumption is not made according to the preferred embodiment.

Figure 2:
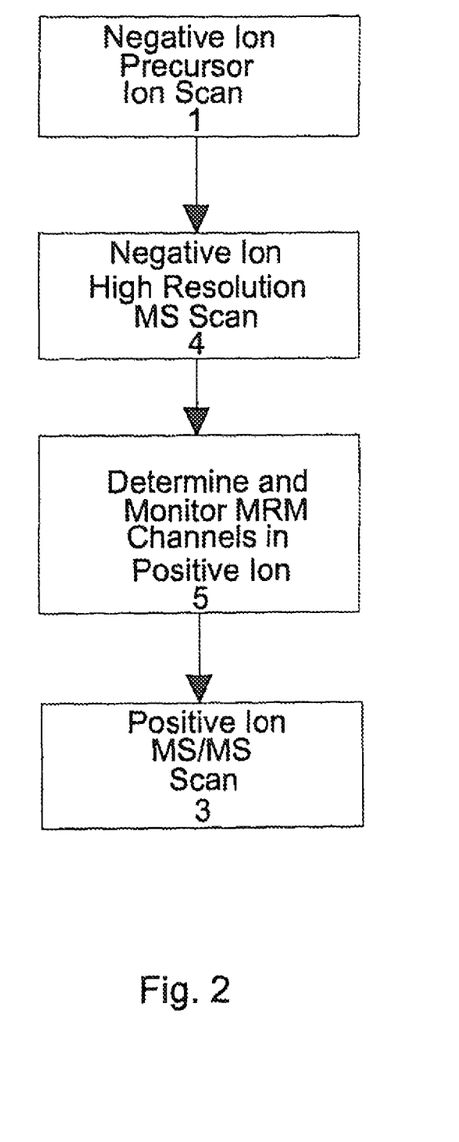
FIG. 2 shows a method of identifying and characterising post translationally modified peptides according to an embodiment of the present invention.

The preferred embodiment of the present invention relates to the analysis of post translationally modified proteins (normally treated by enzymatic or chemical digestion to produce post translationally modified peptides) by liquid chromatography, coupled with a novel acquisition method on a tandem mass spectrometer. The basic concept is shown in FIG. 2 and will be explained below for the case of phosphorylated peptides.

According to an embodiment of the present invention peptides are separated by liquid chromatography and are then arranged to enter an Electrospray Ionisation ("ESI") or a nanoESI ion source of a mass spectrometer ("MS"). The mass spectrometer comprises a first quadrupole mass filter (MS1) followed by a gas filled collision cell arranged downstream of the first quadrupole mass filter. A second quadrupole mass filter (MS2) is arranged downstream of the collision cell. The collision cell is preferably arranged to fragment ions by Collision Induced Dissociation ("CID").

According to other less preferred embodiments the first and/or second quadrupole mass filters may be replaced with other forms of mass filters or one or more mass analysers. The CID collision cell may also be replaced with other forms of fragmentation device including an Electron Transfer Dissociation ("ETD") fragmentation device.

According to a less preferred embodiment, instead of using a triple quadrupole arrangement comprising a first quadrupole mass filter MS1, a quadrupole collision cell and a second quadrupole mass filter or analyser MS2, a hybrid quadrupole-Time of Flight mass spectrometer may be used comprising a quadrupole mass filter/analyser, a fragmentation device and a Time of Flight mass analyser.

In a first step 1 of the preferred embodiment of the present invention as shown in FIG. 2, the mass spectrometer is preferably configured to detect negatively charged fragment ions and is operated in a parent ion or precursor ion scanning mode wherein the second quadrupole rod set MS2 is operated in a resolving mode and is set to transmit only fragment ions which emerge from the collision cell or fragmentation device and which have the mass to charge ratio of the common structural motif. The first mass filter MS1 is set to resolve and is scanned.

According to the preferred embodiment the second quadrupole rod set or second mass filter MS2 may be set to transmit fragment or product ions having a mass to charge ratio of 79 ($PO_3-$). When fragment or product ions having a mass to charge ratio of 79 are detected (for example by breaching a threshold) the method then preferably moves to a second step 4 wherein the instrument is preferably arranged to perform a narrow MS scan still in a negative ion mode in order to determine the mass to charge ratio and charge state of the one or more precursor or parent ion(s). The MS scan 4 is performed either by setting MS1 to resolve and scanning MS1 with MS2 not resolving or vice versa.

The MS scan step 4 is then preferably immediately followed by a third step 5 wherein the mass spectrometer is preferably rapidly switched to a positive ion mode and based upon the information determined from the negative ion mode scans, the instrument preferably determines several multiple reaction monitoring (MRM) channels to monitor. The MRM channels to monitor are calculated based upon the MS information gained from the negative ion experiments (precursor or parent ion mass to charge ratio values) and the assumption that one of the selected ions is phosphorylated and will therefore exhibit either a neutral loss of $H_3PO_4$ or will show a low mass to charge ratio marker ion (immonium ion) for a phosphotyrosine residue (mass to charge ratio 216). Accordingly, MRM channels are selected and monitored. The MRM channels preferably have a narrow width of approximately 0.7 Da at half height.

The signal intensity of these MRM measurements is then preferably consequently used to determine which ion is modified and which is the most intense mass to charge ratio and charge state observed in the positive ion mode. Alternatively, mass scans covering small mass ranges may be acquired as an alternative to setting and monitoring a MRM channel. However, in the claims reference to setting and monitoring MRM channels should be construed as covering embodiments wherein a narrow scan is performed across a narrow mass to charge ratio range.

Finally, in a fourth step 3, a full product ion or MS/MS spectrum is preferably acquired of the phosphorylated peptide to determine the sequence of the peptide and the site of phosphorylation. In this mode of operation MS1 is set to transmit parent ions having a particular mass to charge ratio and the parent ions are then fragmented in the collision cell. The resulting fragment ions are then mass analysed by MS2 which is set to scan.

Figure 3A:
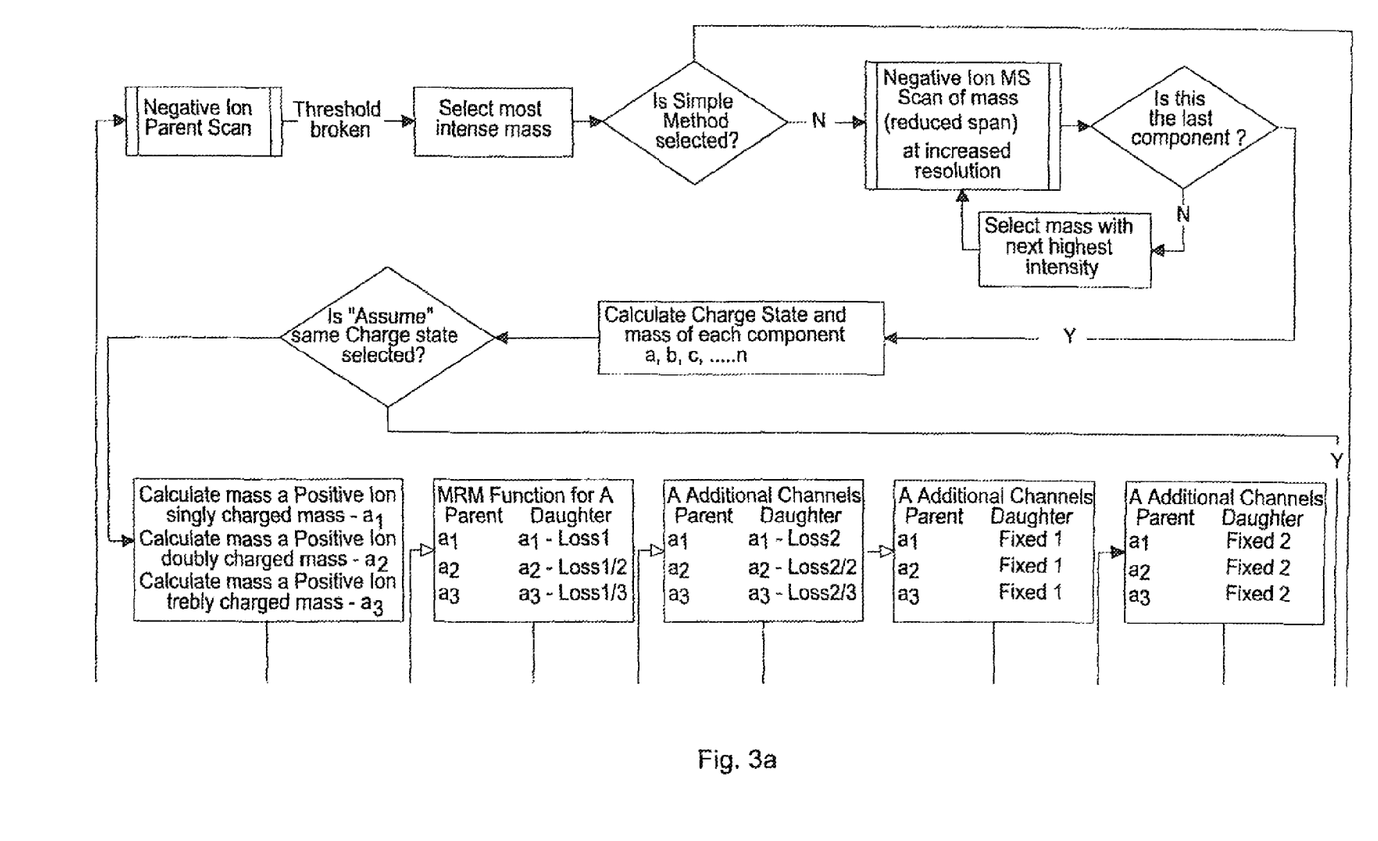
FIGS. 3A-3C shows a comprehensive method of identifying and characterising post translationally modified peptides according to an embodiment of the present invention.
Figure 3B:
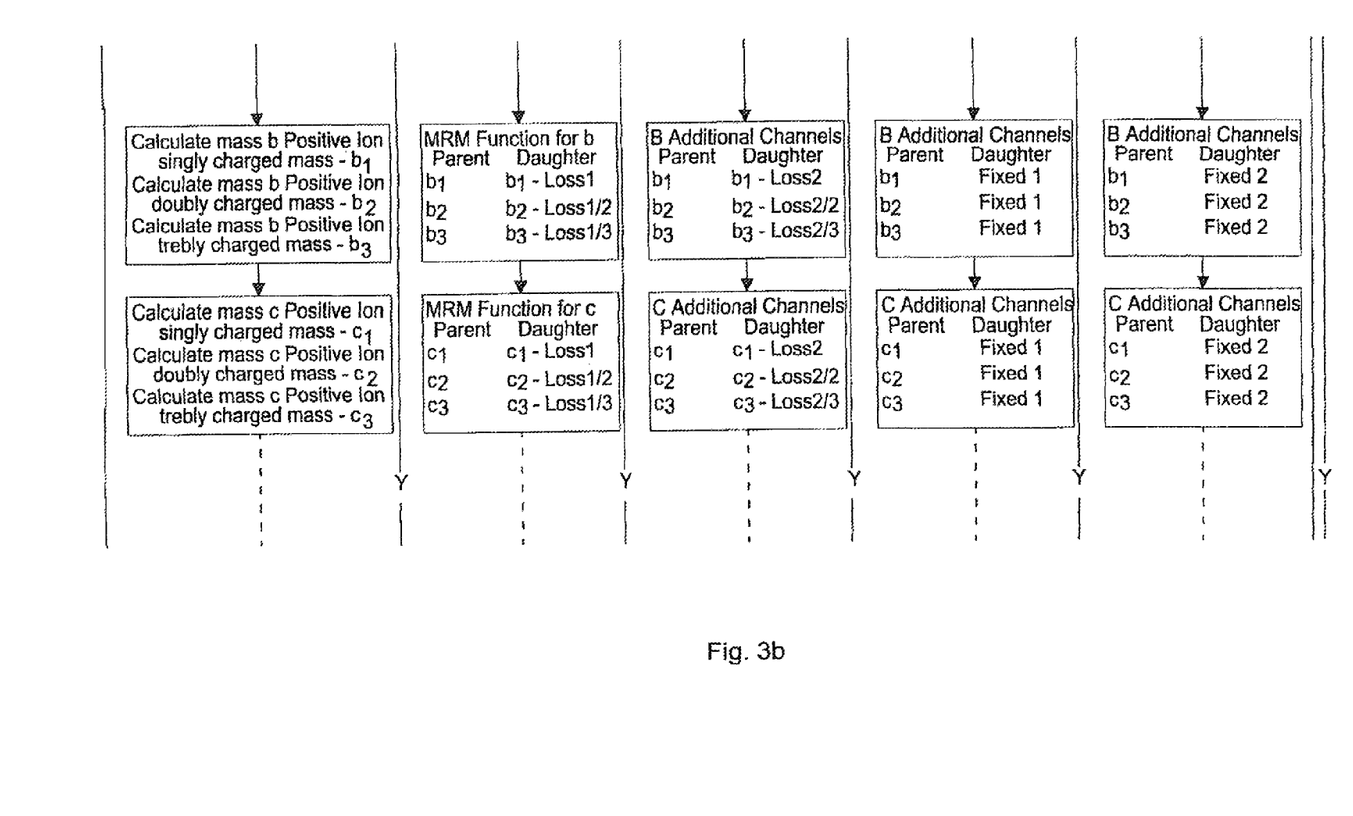
Figure 3C:
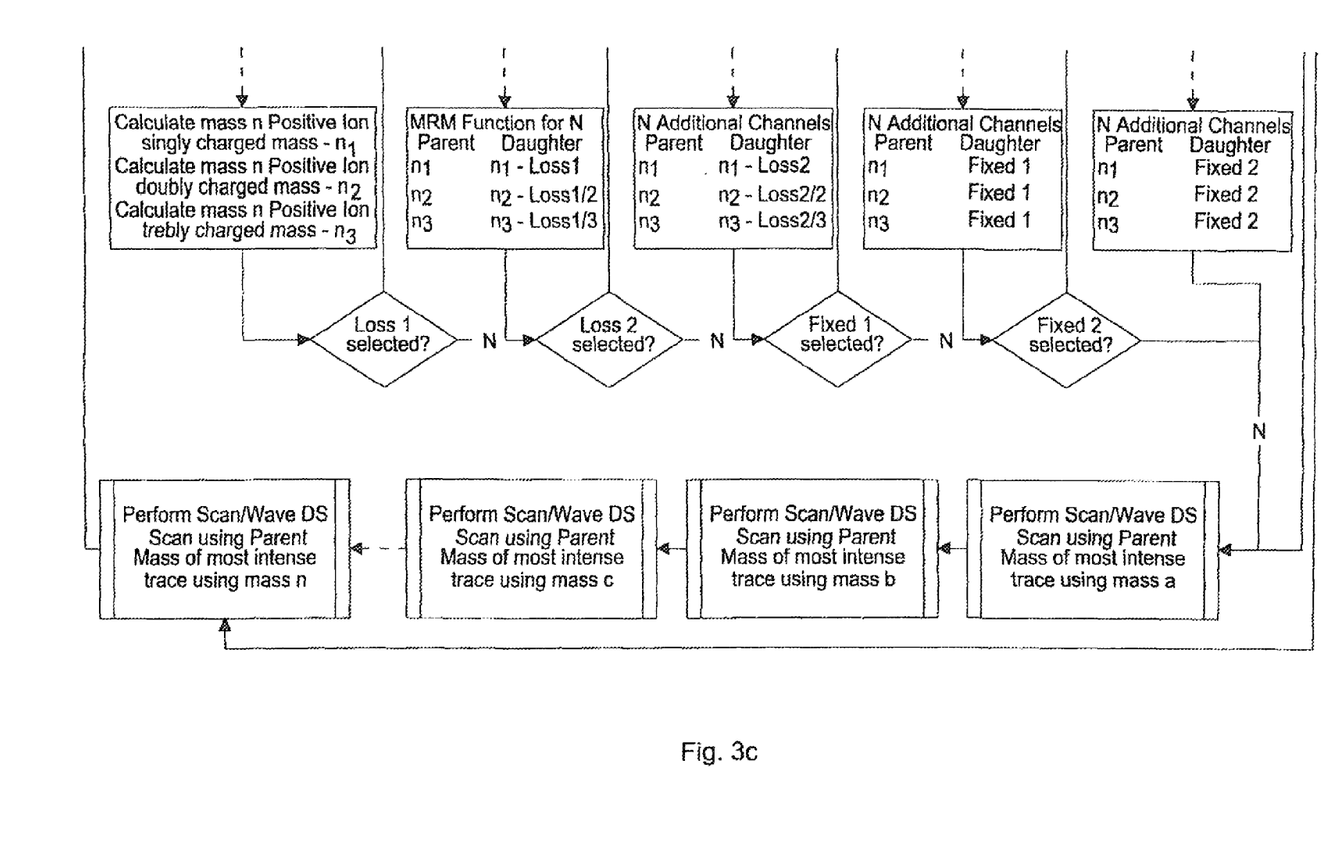

This basic method may be expanded so that multiple components and multiple neutral losses (or gains) can be monitored using the same method. An example flow chart for such a method is shown in FIGS. 3A-3C. In FIG. 3C reference is made to performing a Scan/Wave DS scan. This should be understood as meaning that a MS/MS or daughter ion scan is performed. According to a preferred embodiment the MS/MS scan may be performed using a Scan/Wave® instrument wherein ions are ejected from an ion trap having a single pseudo-potential barrier arranged at the exit of the device. Ions are preferably urged towards the pseudo-potential barrier by applying one or more transient DC voltages to electrodes forming the ion trap so that ions are urged towards the exit of the device. The height of the pseudo-potential barrier may be varied.

According to an embodiment some of the scans or measurements may be performed using a different type of mass analyser, such as a linear ion trap or a Time of Flight mass analyser rather than using a scanning quadrupole.

The PTM detection method according to the preferred embodiment was tested on a XEVO® TQ tandem quadrupole (Waters Corporation, Manchester) using Waters® MPDS Phosphopeptide mixture (186003285). This mixture comprised four phosphopeptides i.e. phosphorylated peptides: (i) NVPL(pY)K; (ii) HLADL(pS)K; (iii) VNQIG(pT)LSESIK; and (iv) VNQIGTL(pS)E(pS)IK. The sample was prepared in 1 mM EDTA and 5 mM Ammonium Phosphate and a Nano-Acquity® UPLC was operated in trapping mode to provide chromatographic separation. Full loop injections of 50 mM EDTA (no gradient) were made prior to each sample injection and the gradient used was 5 to 40% B in 30 mins at 300 nL/min.

In the first stage of the experiment two negative ion precursor scans were performed at different collision energies, 30 eV and 70 eV, monitoring for a fragment ion of 79 Da. The mass spectrometer comprised a first quadrupole mass filter Q1, a collision cell and a second quadrupole mass filter/analyser Q2. The collision energy was fixed by setting an appropriate voltage difference between the first quadrupole Q1 and the collision cell.

Figure 4A:
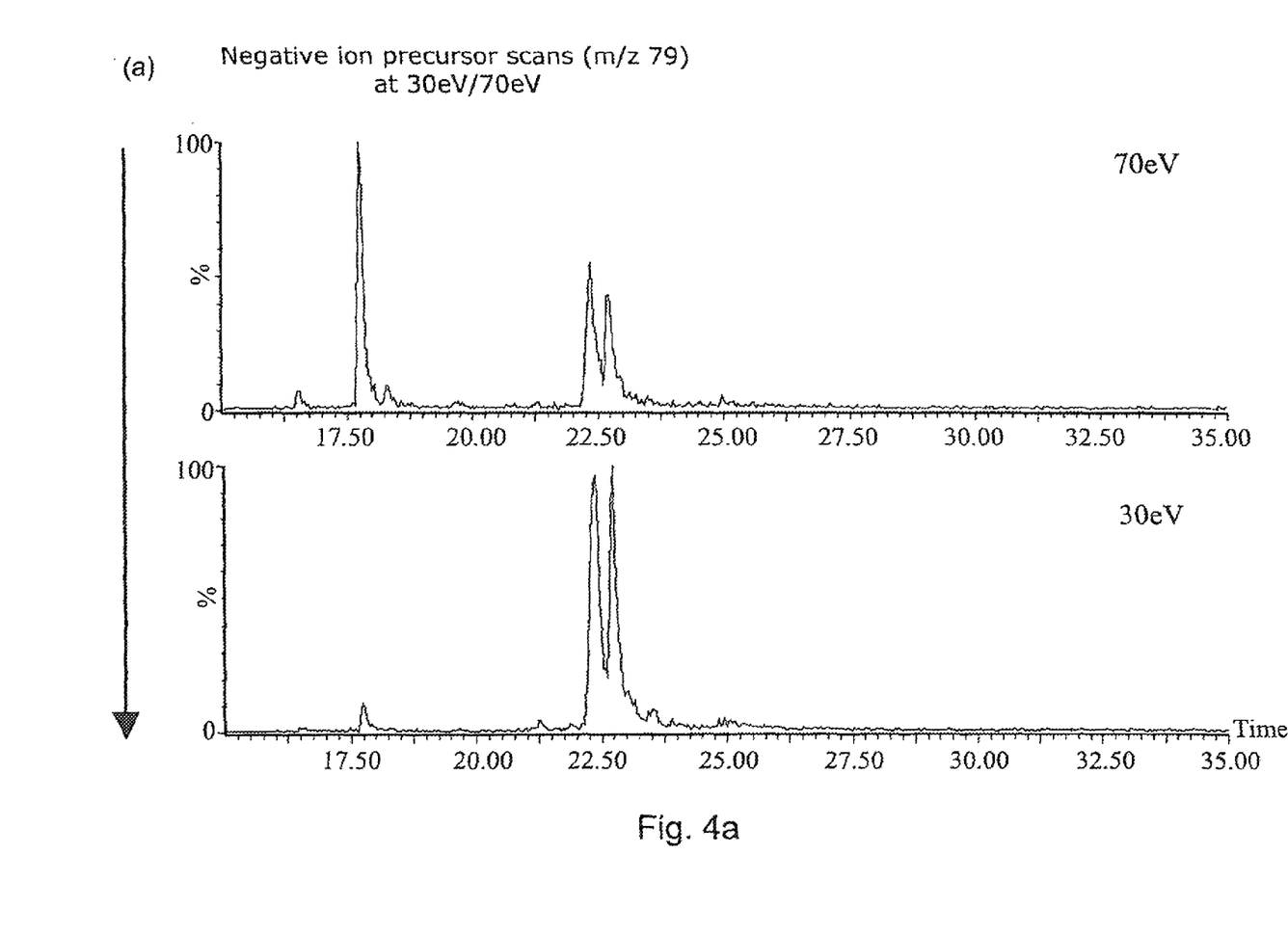
FIG. 4A shows two mass chromatograms corresponding to two negative ion precursor scans performed at 30 eV and 70 eV on a mixture comprising four phosphopeptides (i.e. phosphorylated peptides)

The resulting mass chromatograms for the two different collision energies are displayed in FIG. 4A. At least three out of four peaks are readily observed which correspond with three of the four phosphorylated peptides.

Once the intensity of either scan exceeded a defined threshold a high resolution negative ion MS scan was then performed to determine an accurate mass for each precursor or parent ion in negative ion mode and to determine its charge state.

Figure 4B:
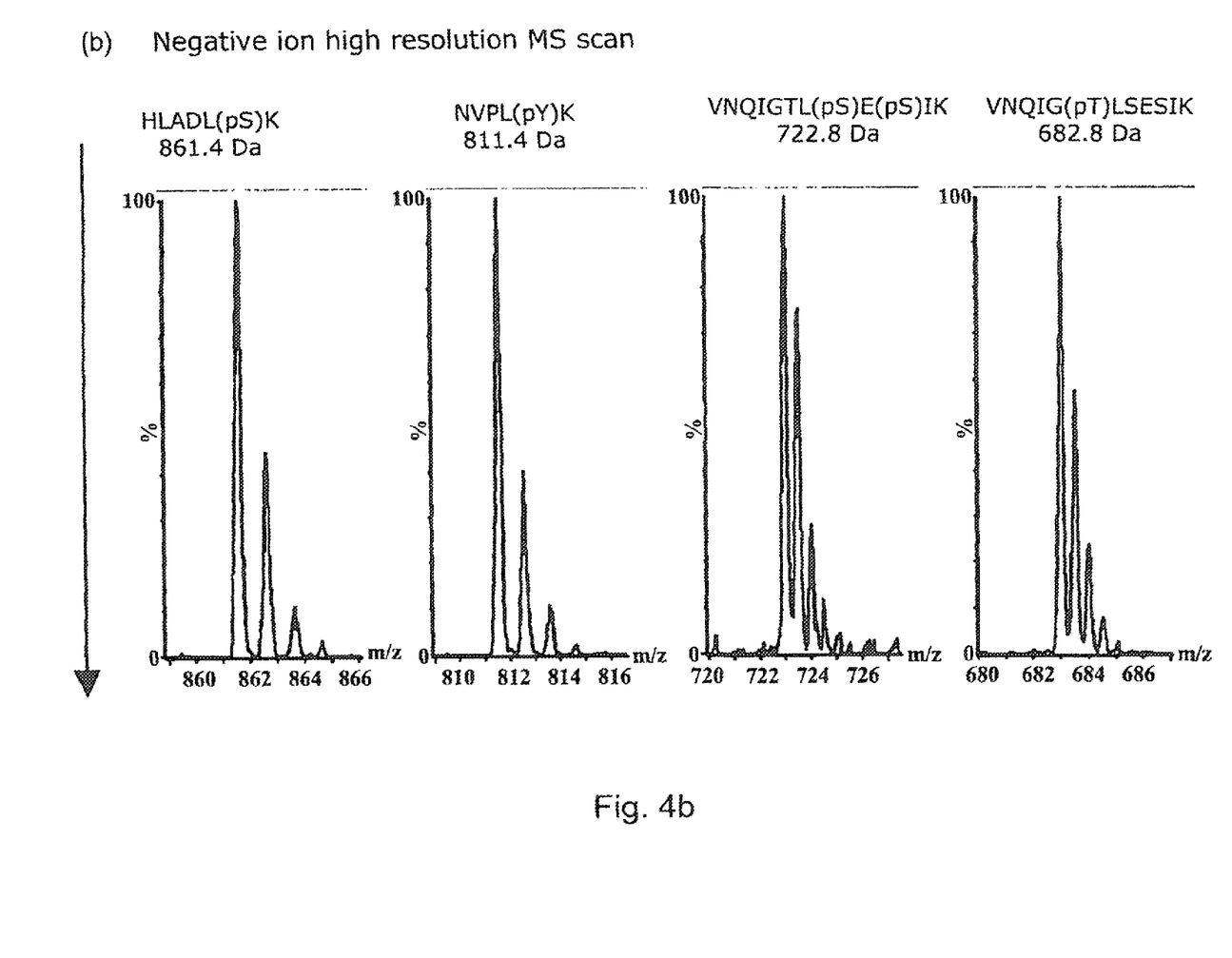
FIG. 4B shows four negative ion high resolution MS scans for the four phosphopeptides.
Figure 4C:
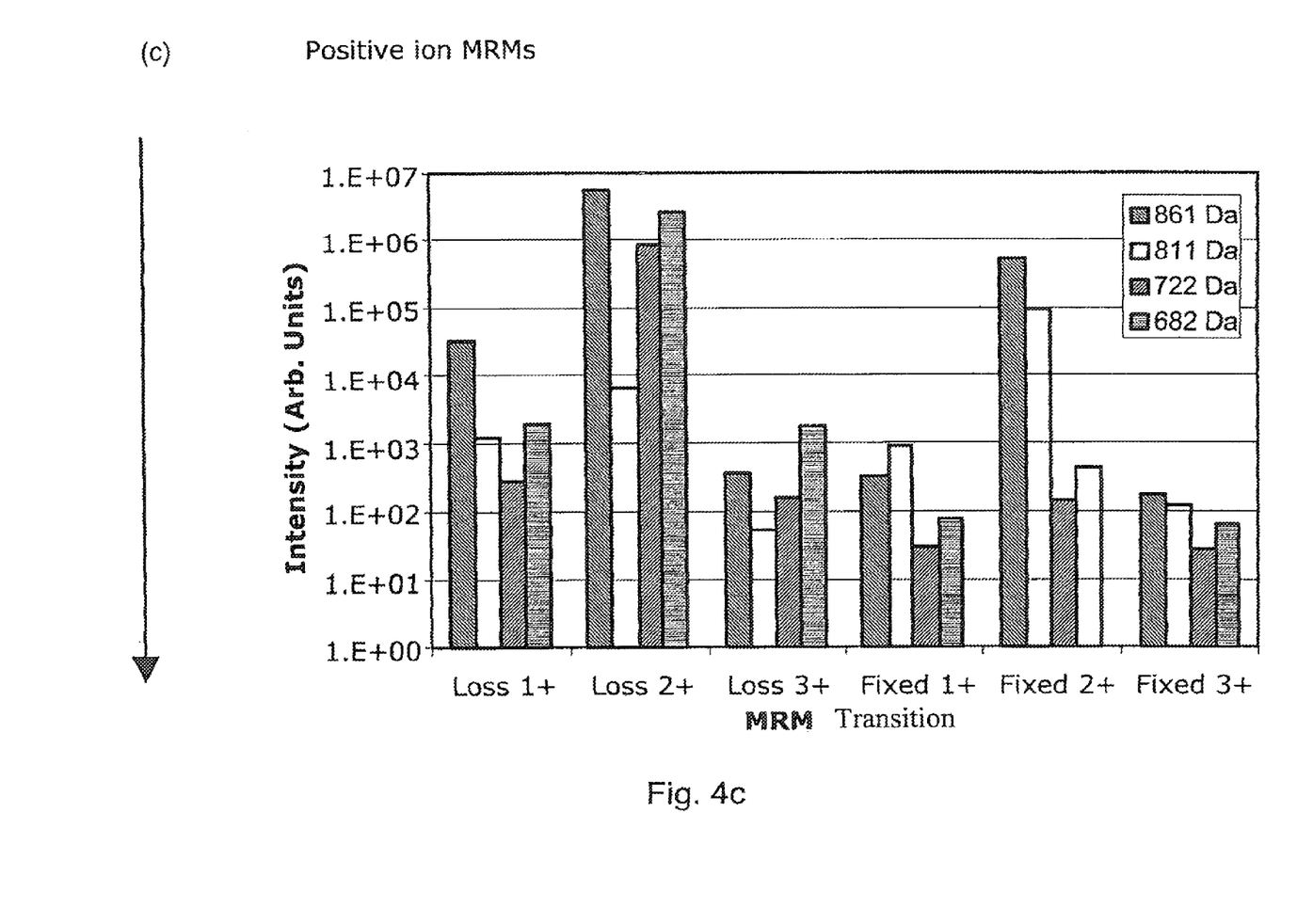
FIG. 4C shows the resultant MRM intensities for six MRM transitions for the four phosphopeptides and FIG. 4D shows a positive ion full scan MS/MS mass spectrum.

FIG. 4B displays the resultant spectra for the four phosphopeptides in this mixture. It is apparent from the istope peak spacing that the first two peptides shown in FIG. 4B are singly charged whereas the third and fourth peptides shown in FIG. 4C are doubly charged peptides.

Using this information, for each possible positive charge state, an MRM transition was set up to look for the neutral loss characteristic of pT and pS phosphopeptides in addition to the characteristic pY immonium ion (m/z 216.1). For example, six MRM transitions were set up and monitored for the m/z 861.4 precursor ion shown in FIG. 4B. These six MRM transitions were as follows:

|          | Precursor m/z        | Product m/z           |
|----------|----------------------|-----------------------|
| Loss 1+: | 863.4 $[M]^+$        | 765.4 $[M]^+$-98      |
| Loss 2+: | 432.2 $[2M]^{2+}$    | 383.2 $[2M]^{2+}$-98/2|
| Loss 3+: | 288.5 $[3M]^{3+}$    | 255.8 $[3M]^{3+}$-98/3|
| Fixed 1+:| 863.4 $[M]^+$        | 216.1                 |
| Fixed 2+:| 432.2 $[2M]^{2+}$    | 216.1                 |
| Fixed 3+:| 288.5 $[3M]^{3+}$    | 216.1                 |

These six MRM transitions were then monitored to identify the most intense charge state of the phosphopeptide in positive ion mode. The resultant MRM intensities for all four phosphopeptides are shown in FIG. 4C. It is important to note that two of the four peptides were singly charged in negative ion mode whereas in all cases the most intense ions were doubly charged in positive ion mode.

Figure 4D:
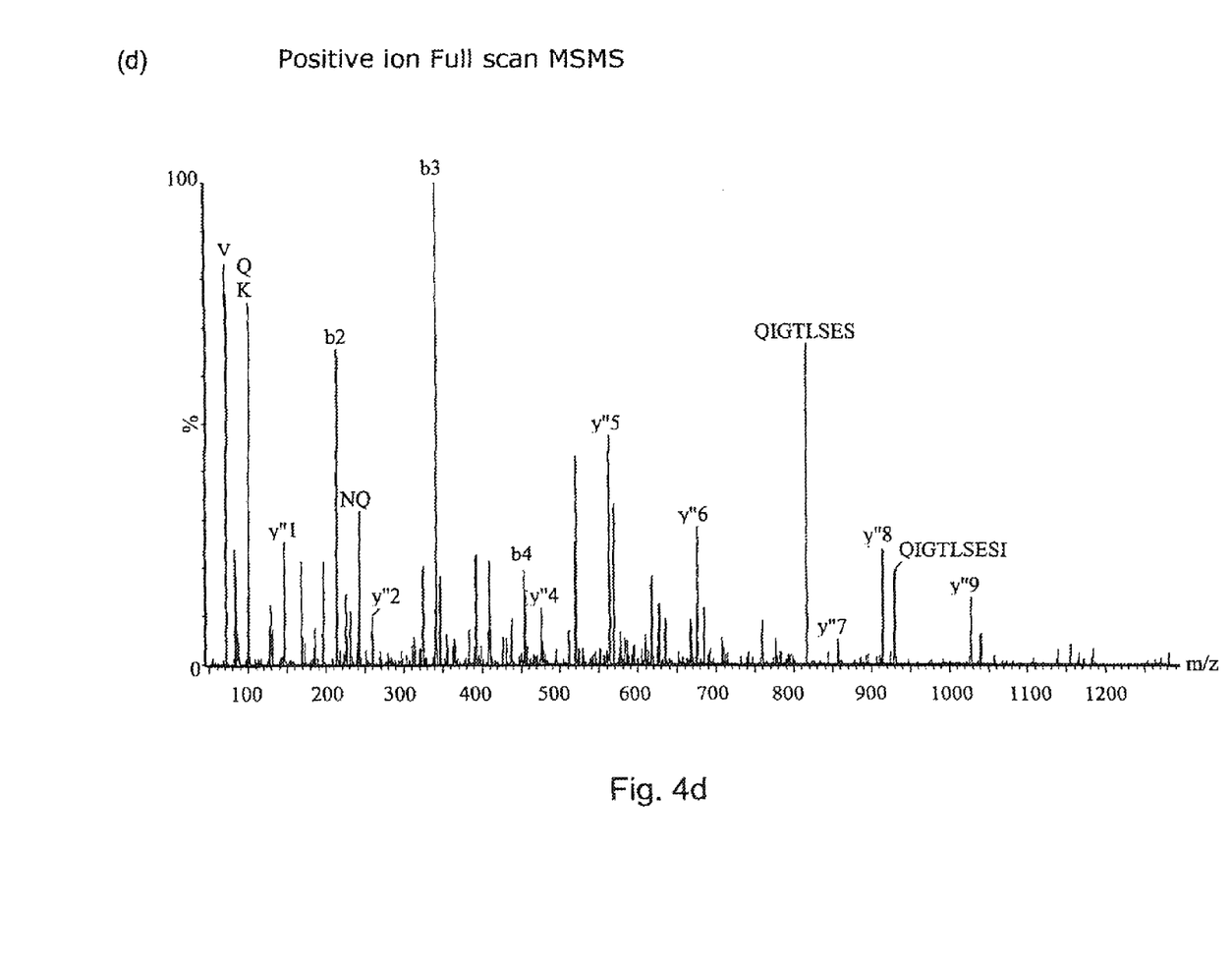

Once the most intense positive ion charge state had been determined, a ScanWave enhanced product ion scan was acquired to allow the sequence of the peptide to be determined as shown in FIG. 4D. As detailed above, a ScanWave product ion scan corresponds essentially with a MS/MS scan and provides a detailed fragment ion spectrum which enables sequence information to be determined thereby enabling identification of the parent ion.

A less preferred embodiment has been referred to above wherein mass scans covering small mass ranges may be acquired as an alternative to a MRM channel. However, reference in the claims to setting and monitoring MRM channels should also be construed as covering embodiments wherein the MRM channel is not precisely fixed but rather where a narrow mass scan is performed over a narrow mass to charge ratio range of, for example, 0.1 Da. Such embodiments are intended to fall within the scope of the claims.

In the claims the phrase "mass to charge ratio transmission window" of a mass filter is used. It is contemplated that according to some less preferred embodiments of the present invention a device other than a conventional quadrupole mass filter may be used to select ions having a particular mass to charge ratio. In such circumstances the device may not operate with a mass to charge ratio transmission window at least in the same sense as a quadrupole mass filter. Accordingly, the use of a mass filter having a mass to charge ratio transmission window is preferred but not essential.

Although the present invention has been described with reference to preferred embodiments, it will be understood by those skilled in the art that various changes in form and detail may be made without departing from the scope of the invention as set forth in the accompanying claims.

The invention claimed is:

1. A method of detecting post translationally modified peptides using mass spectrometry comprising:
   (i) providing a mass spectrometer comprising an ion source, a first mass filter or mass analyser, a collision, fragmentation or reaction device arranged downstream of said first mass filter or mass analyser and a second mass filter or mass analyser arranged downstream of said collision, fragmentation or reaction device;
   (ii) performing a relatively low resolution negative parent ion scan wherein a mass to charge ratio transmission window of said first mass filter or mass analyser is scanned whilst a mass to charge ratio transmission window of said second mass filter or mass analyser is fixed and monitoring for first fragment ions of interest having a first mass to charge ratio above a threshold; wherein if first fragment ions of interest are detected by reaching the threshold then said method further comprises:
   (iii) performing a relatively high resolution negative MS scan wherein a mass to charge ratio transmission window of either said first mass filter or mass analyser or said second mass filter or mass analyser is scanned whilst the other mass filter or mass analyser is operated in a non-resolving mode of operation;
   immediately followed by a step (iv) comprising switching the mass spectrometer to a positive ion mode and, based upon information determined from the negative ion mode scans and expected phosphorylation, determining with the mass spectrometer at least a first positive ion Multiple Reaction Monitoring channel corresponding to positive ions having a first positive charge state, a second positive ion Multiple Reaction Monitoring channel corresponding to positive ions having a second positive charge state and a third positive ion Multiple Reaction Monitoring channel corresponding to positive ions having a third positive charge state;
   setting and monitoring at least said first, second and third positive ion Multiple Reaction Monitoring channels and determining which Multiple Reaction Monitoring channel results in a highest intensity of observed ions; and determining a mass to charge ratio or charge state of parent ions which correspond with the Multiple Reaction Monitoring channel which resulted in the highest intensity of observed ions; and
   a step (v) of performing a MS/MS scan wherein a mass to charge ratio transmission window of said first mass filter or mass analyser is set so as to correspond with the a mass to charge ratio transmission window at which said first mass filter or mass analyser was set for the Multiple Reaction Monitoring channel which resulted in the highest intensity of observed ions, and wherein a mass to charge ratio transmission window of said second mass filter or mass analyser is scanned to detect post translationally modified peptides.

2. A method as claimed in claim 1, wherein said Multiple Reaction Monitoring channels are arranged to have a mass to charge ratio width of x Da at half height, wherein x is selected from a group consisting of: (i)<0.1; (ii) 0.1-0.2; (iii) 0.2-0.3; (iv) 0.3-0.4; (v) 0.4-0.5; (vi) 0.5-0.6; (vii) 0.6-0.7; (viii) 0.7-0.8; (ix) 0.8-0.9; and (x) 0.9-1.0.

3. A method as claimed in claim 1, further comprising ionising ions using an ion source selected from a group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; and (xviii) a Thermospray ion source.

4. A method of mass spectrometry as claimed in claim 1, further comprising temporally separating analyte ions of interest using a liquid chromatography device prior to ionising said analyte ions using an ion source.

5. A method of mass spectrometry as claimed in claim 1, wherein said collision, fragmentation or reaction device is selected from a group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an ion-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; and (xxviii) an ion-metastable atom reaction device for reacting ions to form adduct or product ions.

6. A method as claimed in claim 1, wherein said step of setting and monitoring at least said first, second and third positive ion Multiple Reaction Monitoring channels comprises fixing said Multiple Reaction Monitoring channels or performing narrow mass scans over a narrow mass to charge ratio range.

7. A method as claimed in claim 1, wherein steps i-v are performed as successive steps in a continuous experiment.

* * * * *